United States Patent
Fei et al.

(10) Patent No.: US 9,801,940 B2
(45) Date of Patent: Oct. 31, 2017

(54) ORAL CARE COMPOSITIONS

(75) Inventors: Lin Fei, Kendall Park, NJ (US); Ravi Subramanyam, Mumbai (IN); Guofeng Xu, Plainsboro, NJ (US)

(73) Assignee: Colgate-Palmolive Company, New York, NY (US)

( * ) Notice: Subject to any disclaimer, the term of this patent is extended or adjusted under 35 U.S.C. 154(b) by 13 days.

(21) Appl. No.: 13/575,671

(22) PCT Filed: Feb. 24, 2011

(86) PCT No.: PCT/US2011/026017
§ 371 (c)(1),
(2), (4) Date: Jul. 27, 2012

(87) PCT Pub. No.: WO2011/106492
PCT Pub. Date: Sep. 1, 2011

(65) Prior Publication Data
US 2012/0294812 A1    Nov. 22, 2012

Related U.S. Application Data

(60) Provisional application No. 61/307,664, filed on Feb. 24, 2010.

(51) Int. Cl.
| | | |
|---|---|---|
| *A61K 36/575* | (2006.01) | |
| *A61G 11/00* | (2006.01) | |
| *A61K 47/10* | (2017.01) | |
| *A61K 8/34* | (2006.01) | |
| *A61K 8/97* | (2017.01) | |
| *A61K 9/00* | (2006.01) | |
| *A61Q 11/00* | (2006.01) | |

(52) U.S. Cl.
CPC .............. *A61K 47/10* (2013.01); *A61K 8/347* (2013.01); *A61K 8/97* (2013.01); *A61K 9/006* (2013.01); *A61K 36/575* (2013.01); *A61Q 11/00* (2013.01)

(58) Field of Classification Search
CPC ............................. A61K 36/575; A61Q 11/00
See application file for complete search history.

(56) References Cited

U.S. PATENT DOCUMENTS

| | | | |
|---|---|---|---|
| 6,544,409 B2 | 4/2003 | DeSouza | |
| 7,608,741 B2 | 10/2009 | Kim et al. | |
| 2006/0127329 A1 | 6/2006 | Xu et al. | |
| 2006/0134024 A1* | 6/2006 | Trivedi | A61K 8/347 424/58 |
| 2006/0140880 A1* | 6/2006 | Subramanyam et al. | 424/49 |
| 2006/0140885 A1 | 6/2006 | Gaffar et al. | |
| 2009/0087501 A1 | 4/2009 | Cummins | |

FOREIGN PATENT DOCUMENTS

| | | | |
|---|---|---|---|
| CN | 1331968 | 1/2002 | |
| CN | 101222909 | 7/2008 | |
| DE | WO 2008006582 A1 * | 1/2008 | ............ A61K 8/347 |
| RU | 2270668 C2 | 2/2006 | |
| WO | WO 97/35599 | 10/1997 | |
| WO | WO 97/35599 A1 | 10/1997 | |
| WO | WO 01/82922 | 11/2001 | |
| WO | WO 01/85116 A2 | 11/2001 | |
| WO | WO 0185116 A2 * | 11/2001 | ............ A61K 8/347 |
| WO | WO 04/000235 | 12/2003 | |
| WO | WO 2004000235 A2 * | 12/2003 | ............... A23G 3/36 |
| WO | WO 2006/065403 | 6/2006 | |
| WO | WO 2006/071653 | 7/2006 | |

OTHER PUBLICATIONS

Fordyce et al., "Studies on Reactions Relating to Carbohydrates and Polysaccharides. LVI. The Synthesis of the Higher Polyoxyethylene Glycols," J. Am. Chem. Soc., 1939, 61:1905-1910.
Patocka et al., "Expectations of biologically active compounds of the genus *Magnolia* in biomedicine," J. Appl. Biomed., 2006, pp. 171-178, vol. 4, No. 4.
Powell, "Chapter 18—Polyethylene Glycol," Handbook of Water-Soluble Gums and Resins, 1980, pp. 18/1-18/31, R.L. Davidson ed. (McGraw-Hill, New York).
International Search Report issued for corresponding International Application No. PCT/US2011/026017 mailed on May 24, 2011.
Huang et al., 2002, "Research Progress of Botanicals for Caries Prevention," Chinese J. Conservative Dentistry 12(10):574-576.
Lu et al., 1993, "Preparation and Application of Officinal Magnolia Bark Gargle," China J. Hospital Pharmacy 13(10):441-442.
Bernaskova, et al., Molecules, 2014, 19, 1223-1237, "Synthesis of tetrahydrohonokiol derivatives and their evaluation for cytotoxic activity against CCRF-CEM leukaemia, U251 glioblastoma and HCT-116 colon cancer cells".
Huang Bingbing, "Research Progress of Botanicals for Caries Prevention," Chinese Journal of Conservative Dentistry, Oct. 2002, vol. 12, No. 10, pp. 574-576.

* cited by examiner

Primary Examiner — Tracy Liu

(57) ABSTRACT

Disclosed herein are methods of enhancing the solubility and delivery of one or more active ingredients found in *magnolia* extract, or a synthetic analog thereof, in an oral composition.

10 Claims, No Drawings

ORAL CARE COMPOSITIONS

CROSS REFERENCE TO RELATED APPLICATIONS

This application is a national stage entry under 35 U.S.C. §371 of International Patent Application No. PCT/US2011/026017, filed on Feb. 24, 2011, which claims priority to U.S. Provisional Patent Application No. 61/307,664, filed on Feb. 24, 2010, which are incorporated herein by reference.

BACKGROUND

There is often an undesired interaction between the active ingredients of *magnolia* extract (or synthetic analogues thereof) and components of the delivery vehicles used to formulate conventional oral compositions of *magnolia* extract that reduces the effective performance of such oral compositions. Consequently, there exists a need to enhance the solubility and positive interaction of the active ingredients of *magnolia* extract or their synthetic analogue compounds with other components in oral compositions. A need also exists for enhancing the efficacy of the delivery of the active ingredients of *magnolia* extract or their synthetic analogue compounds in oral compositions to improve the efficiency and bioavailability of these active ingredients.

SUMMARY

Some embodiments of the present invention provide a method of enhancing the solubility of an active ingredient found in *magnolia* extract, comprising admixing propylene glycol with the active ingredient. In some embodiments, one or more active ingredients are found in *magnolia* extract. In some embodiments, at least one of the one or more active ingredients found in *magnolia* extract is selected from: magnolol; honokiol; tetrahydromagnolol (5,5'-dipropylbiphenyl-2,2'-diol); tetrahydrohonokiol (3',5-dipropylbiphenyl-2,4'-diol); n-butyl magnolol (5,5'-dibutylbiphenyl-2,2'-diol); and a combination of two or more thereof. Some embodiments of the present invention provide a method of enhancing the solubility of a synthetic analogue of an active ingredient found in *magnolia* extract, comprising admixing propylene glycol with the synthetic analogue. In some embodiments, the synthetic analogue is selected from isopropyl magnolol, isobutyl magnolol and dichloromagnolol. In some embodiments, the active ingredient and propylene glycol are mixed with an orally acceptable carrier.

In other embodiments, the invention provides an oral composition comprising an active ingredient found in *magnolia* extract or a synthetic analogue thereof; propylene glycol; and an orally acceptable carrier.

Further embodiments provide a method of treating a disease or condition of the oral cavity comprising: providing a composition comprising an active ingredient found in *magnolia* extract or a synthetic analogue thereof; propylene glycol; and an orally acceptable carrier; and applying the composition to the oral cavity of a subject in need thereof. In some embodiments, the composition is applied to the oral cavity daily for a period of one week. In some embodiments, the composition is applied to the oral cavity for up to 2 weeks. In some embodiments, the composition is applied to the oral cavity for a period lasting more than 2 weeks.

DETAILED DESCRIPTION

The methods and compositions of the present embodiments impart advantages over the prior art compositions by providing an oral composition that is well solubilized, safe, and highly efficacious against bacterial infection and/or inflammation in a mammalian subject. Further, some embodiments of the present invention comprise one or more of the active ingredients of *magnolia* extract.

The expressions "carrier" or "aqueous carrier" or "orally acceptable carrier" as used throughout this description denote any safe and effective materials for use herein. Such materials include, water, solvents, etc., that may contain a humectant such as glycerin, sorbitol, xylitol and the like. The carrier or orally acceptable carrier also may include additional dentifrice components, such as thickening agents, ionic active ingredients, buffering agents, anticalculus agents, abrasive polishing materials, peroxide sources, alkali metal bicarbonate salts, surfactants, titanium dioxide, coloring agents, flavor systems, sweetening agents, antimicrobial agents, herbal agents, desensitizing agents, stain reducing agents, and mixtures thereof.

All percentages and ratios used herein are by weight of the oral care composition, unless otherwise specified. All measurements are made at 25° C., unless otherwise specified.

Throughout this description and claims, the disclosure of a certain numerical value (e.g., temperature, weight percent of components, etc.) is meant to denote that value, plus or minus an additional value that would be understood by persons having ordinary skill in the art, depending on the variable and the degree of measurement error typically associated with that value. For example, a given temperature would be understood by a person having ordinary skill in the art to include up to 10% variability, given the instrument used to measure the temperature.

Some embodiments of the present invention provide a method for enhancing the solubility of one or more active ingredients found in *magnolia* extract or a synthetic analogue thereof, in an oral composition. In some embodiments, the method comprises admixing an effective amount of propylene glycol with one or more of the active ingredients found in *magnolia* extract or a synthetic analogue thereof. In some embodiments, at least one of the one or more active ingredients found in *magnolia* extract is selected from: magnolol, honokiol, tetrahydromagnolol, tetrahydrohonokiol (3',5-dipropylbiphenyl-2,4'-diol), 5,5'-di-n-butyl-biphenyl-2,2'-diol, n-butyl magnolol (5,5'-dibutylbiphenyl-2,2'-diol). In some embodiments, the synthetic analogue of an active compound of *magnolia* extract is selected from: isopropyl magnolol; isobutyl magnolol; and dichloromagnolol. In some embodiments, the orally acceptable carrier does not contain propylene glycol as a humectant. In other embodiments, the orally acceptable carrier contains propylene glycol.

Some embodiments comprise a method of making a solubilized oral composition by mixing: from 0.05 to 10% by weight propylene glycol with at least one of the one or more active ingredients found in *magnolia* extract or a synthetic analogue thereof; and an orally acceptable carrier. In some embodiments, the propylene glycol comprises from 0.1 to 5% by weight of the composition. In other embodiments, at least one of the one or more active ingredients found in *magnolia* extract, or a synthetic analogue thereof, is present in the amount of from 0.05 to 5% by weight of the composition, preferably from 0.1 to 3% by weight of the composition.

Further embodiments of the present invention provide an oral composition comprising: (i) an effective amount of propylene glycol; (ii) at least one of the one or more active ingredients found in *magnolia* extract, or a synthetic analogue thereof; and (iii) an orally acceptable carrier. In some embodiments, the oral composition is an oral care composition.

In some embodiments, the compositions are used to inhibit the excess production of cellular mediators of inflammation in oral tissues at sites of inflammation caused by infection, environmental toxins, or trauma in the oral cavity. In some embodiments, an effective amount of at least one of the one or more active ingredients found in *magnolia* extract, or a synthetic analogue thereof, reduces the levels or activity of proinflammatory mediators adequately to reduce the concentration in the mammalian subject to basal levels in the oral tissue of the subjects treated, without unnecessarily suppressing all intercellular mediator activity.

In some embodiments, at least one of the one or more active ingredients found in *magnolia* extract, or a synthetic analogue thereof, will be present in the amount required to have the desired therapeutic or prophylactic effect in the human or lower animal subject to whom the active is administered, without undue adverse side effects (such as toxicity, irritation, or allergic response), commensurate with a reasonable benefit/risk ratio when used in the manner of this invention. The specific safe and effective amount of the active ingredients will vary with such factors as the particular condition being treated, the physical condition of the subject, the nature of concurrent therapy (if any), the specific compound used, the specific dosage form, the carrier employed, and the desired dosage regimen. Those skilled in the art will be capable of determining a safe and effective amount of active ingredient to use in the compositions and methods, using the guidelines provided herein.

In highly sensitive tissue, high concentrations of *magnolia* may potentially cause irritation and exacerbate inflammation, rather than reduce it. While the potential for additional inflammation is dependent upon the individual subject's status and response to irritants, as well as other variables related to treatment, it is preferred that the one or more active ingredients found in *magnolia* extract, or the synthetic analogue thereof, is provided to the subject at a non-irritating concentration. By "non-irritating" it is meant that the contact of the oral composition with the oral cavity of a mammalian subject does not increase soreness, pain, redness, or roughness, nor does it exacerbate or worsen inflammation of the oral tissue.

In addition, the concentration of the one or more active ingredients found in *magnolia* extract, or a synthetic analogue thereof, in the oral composition will vary depending on delivery form, dosage regimen, end benefits, pathology, and/or the individual therapeutic requirements of the subject(s) to whom it is administered, and as such, it is contemplated that the amount of active ingredient present may vary as recognized by one of skill in the art. Additionally, the concentration of the active ingredients is typically dependent upon the form of the oral composition. For example, mouthrinses typically have a relatively low concentration of an active ingredient, whereas dentifrices, gels, or toothpowders have a higher concentration to achieve the same delivered dosage based on ease of dispersion. Likewise, confectionary compositions typically have a relatively high concentration of active ingredient to enable sufficient dispersion as they dissolve or are masticated.

The term "confectionery composition" as used herein includes chewing gums, and orally dissolvable tablets, beads, and lozenges. Saliva dissolves the lozenge or chewable gum product, and promotes prolonged contact with oral surfaces so that the active ingredient in a lozenge, tablet, bead or chewing gum form is adequately delivered to the oral surface targeted, when the product is used.

As referred to herein, the expressions "extract of *magnolia*" or "*magnolia* extract" denote an extract from dried cortex, or bark, of a plant from the Magnoliaceae family, such as *Magnolia officinalis*, (hereinafter "*magnolia*"), or a synthetic or semi-synthetic equivalent of such an extract or an active component thereof. In certain embodiments, the oral composition comprises one or more active ingredients that have been isolated from an extract of *magnolia* or made by conventional synthetic methods. In other embodiments, the oral composition comprises an extract of *magnolia*. Preferably, extracts of *Magnolia* Cortex (the bark of *Magnolia officinalis*) contain active compounds including: magnolol, honokiol, tetrahydromagnolol (5,5'-dipropylbiphenyl-2,2'-diol), and tetrahydrohonokiol (3',5-dipropylbiphenyl-2,4'-diol), which have demonstrated bactericidal properties against representative oral bacteria *S. mutans, F. nucleatum, V. parvula, A. naslundii, P. gingivitis* in in vitro tests. It should be noted that any plant from the Magnoliaceae family is suitable for extracting the active ingredients used in the present embodiment.

In some embodiments, the extract contains an antimicrobially effective concentration of a compound selected from the group consisting of magnolol, honokiol, tetrahydromagnolol, tetrahydrohonokiol (3',5-dipropylbiphenyl-2,4-diol), isopropyl magnolol, isobutyl magnolol, and n-butyl magnolol (5,5'-dibutylbiphenyl-2,2'-diol), and a combination of two or more thereof. In other embodiments, the oral composition comprises one or more active ingredients selected from the group consisting of: magnolol, honokiol, tetrahydromagnolol, tetrahydrohonokiol (3',5-dipropylbiphenyl-2,4'-diol), n-butyl magnolol (5,5'-dibutylbiphenyl-2,2'-diol), and a combination of two or more thereof; in an amount effective to treat bacterial and/or inflammation related oral conditions in a mammalian subject.

In some embodiments, the *magnolia* extract can be prepared by way of extraction. In one method of extraction, the dried, crushed *Magnolia* bark in the form of a powder is sequentially contacted with ethanol, methylene chloride, and cyclohexane to form in each step a concentrated paste, the last paste form being dissolved in heated petroleum ether at about 50°-60° C., and then dried under vacuum, the final extraction yielding an extract containing about 5 to about 10% by weight honokiol and about 15 to about 25% by weight magnolol.

In another method of extraction, the *Magnolia* extract is prepared from dried *Magnolia* plant bark and can be made by extracting the bark using an appropriate solvent. Preferred solvents include methanol, ethanol, methylene chloride, hexane cyclohexane, pentane, petroleum ether, chloroform, hydrochloric acid, ethylene dichloride, and hydrofluoroalkanes, such as 1,1,1,2-tetrafluoroethane or HFA-13A. Generally, one part of plant tissue (dry basis) is extracted with 5 to 50 parts, preferably 15 parts to 30 parts of solvent using an extraction apparatus where the solvent is contacted with the bark to obtain a concentrated paste which is then subjected to one or more additional extraction steps with different solvents to further concentrate the originally obtained paste over an extended period of time, preferably about 6 hours to about 1-2 days, more preferably for about 1 day. In one simplified method of extraction, the dried, crushed *Magnolia* bark in the form of a powder is contacted with a hydrofluoroalkane (such as, 1,1,1,2-tetrafluoroethane (HFA-13A)) to form a concentrated final extraction yielding an extract containing 5 to 50% honokiol and 5 to 50% magnolol.

In yet another method of extraction, the *magnolia* extract is isolated by supercritical fluid extraction (SFE) using carbon dioxide ($CO_2$). Supercritical fluids are gases with properties between that of a "normal" phase of gas and liquid. Pressure variations control the properties of the supercritical fluids, which can range from more gas-like behavior to more liquid-like behavior, depending on the application. Supercritical fluids use a solvent that is readily available, inexpensive, and environmentally safe ($CO_2$ and $H_2O$. Carbon dioxide is non-toxic, non-explosive, readily available and easily removed from the extracted products. Process temperatures for SFE are generally low to moderate. Thus, SFE produces nearly solvent-free products, and further avoid any potential deterioration reactions.

Additionally, natural contaminants that may be potentially present in other extraction methodologies are generally absent in the SFE extracted product. For example, compounds such as aristocholic acid and alkaloids, such as magnocurine and tubocurarine, are maintained at low concentrations (for example, generally less than 0.0002 percent). Thus, in the embodiment where the *magnolia* is extracted by SFE, the extract is substantially free from chemical alterations brought about by heat and water, from solvent residues, and other artifacts.

As used herein, "extracting" or "extraction" of a solid or liquid material means contacting the material with an appropriate material, such as a solvent to remove the substance(s) desired to be extracted from the material. Such an extraction may be carried out by conventional means known to one of skill in the art, for example, by using an extraction apparatus, such as a Soxhlet apparatus, which retains the solid material in a holder and allows the solvent to flow through the material; or by blending the solvent and material together and then separating the liquid and solid phases or two immiscible liquid phases, such as by filtration or by settling and decanting.

In various methods of extraction, the *magnolia* extract of the present invention may be comprised of magnolol from 2% to 95%. In some embodiments, the magnolol may be present in the extract from 5 to 50%. In other embodiments, magnolol may be present in the extract from 30 to 50%. In certain embodiments, the honokiol may be present in the extract from 2 to 95%. In further embodiments, the honokiol may be present in the extract from 5 to 50%. In yet other embodiments, honokiol may be present in the extract from 30 to 50%.

In certain embodiments, it is preferred that the active ingredients of *magnolia* extract comprise either magnolol, honokiol, or both. Magnolol and honokiol are non-ionic hydroxybiphenyl compounds, the structures of which are represented as follows:

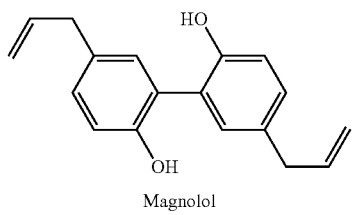

Magnolol

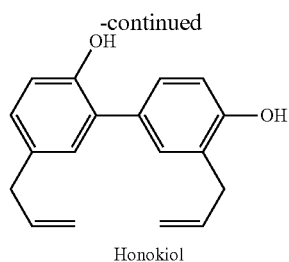

Honokiol

Additionally, tetrahydromagnolol (5,5'-dipropylbiphenyl-2,2'-diol) and tetrahydrohonokiol (3',5-dipropylbiphenyl-2,4'-diol) are hydrogenated analogues of magnolol and honokiol, respectively, and they are often found in the extracts of *magnolia*, and as such may be included in the oral composition. Furthermore, 5,5% dibutylbiphenyl-2,2'-diol (homolog of magnolol), may be also included in the oral composition, and the synthesis of this compound can be achieved through conventional organic synthesis by a person of ordinary skill in the art. The structures of tetrahydromagnolol (5,5'-dipropylbiphenyl-2,2'-diol), tetrahydrohonokiol (3',5-dipropylbiphenyl-2,4'-diol) and 5,5'-di-n-butylbiphenyl-2,2'-diol (homolog of magnolol) are shown below.

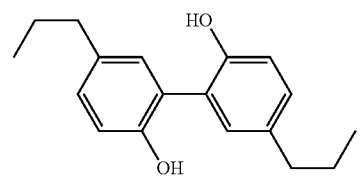

tetrahydromagnolol

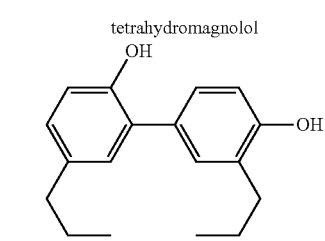

tetrahydrohonokiol

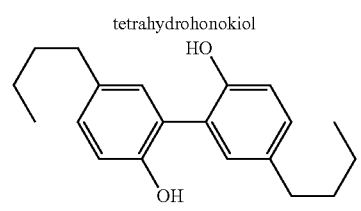

5,5'-di-n-butyl-biphenyl-2,2'-diol

Orally acceptable carriers for use in the invention include the conventional and known carriers used in making toothpastes, tooth powders, prophylaxis pastes, mouth rinses, lozenges, gums, beads, and the like, and are more fully described hereinafter. It is preferred that the orally acceptable carrier does not cause irritation, swelling or pain and does not typically produce an allergic or untoward reaction such as gastric upset, nausea or dizziness. Selection of specific carrier components is dependant on the desired product form, including dentifrices, toothpastes, tooth powders, prophylaxis pastes, mouth rinses, lozenges, gums, gels, paints, confectionaries, and the like.

The term "mouthrinse" in the present invention refers to oral compositions that are substantially liquid in character, such as a mouth wash, spray, or rinse. In such a preparation the orally acceptable carrier typically has an aqueous phase comprising water or a water and alcohol mixture. Further, in various embodiments, the oral carrier includes a humectant and surfactant as described below. Generally, the weight ratio of water to alcohol is in the range of in an amount of 1:1 to 20:1, preferably 3:1 to 10:1 and more preferably 4:1 to 6:1. The total amount of water-alcohol mixture in this type of preparation is typically in an amount of 70 to 99.9% of the preparation. In various embodiments, the alcohol is typically ethanol or isopropanol.

As recognized by one of skill in the art, the orally acceptable carrier of the present invention may also comprise a variety of other conventional active ingredients known to one of skill in the art, including anti-plaque agents, whitening agents, antibacterial agents, tartar control (anti-calculus) agent, anti-caries agents, sensitivity agents, and the like. Preferably, the carrier does not substantially reduce the efficacy of the anti-inflammatory and antibacterial active ingredients found in *magnolia* extract, or synthetic analogues thereof.

The pH of such liquid and other preparations of the oral composition of the present invention is generally in an amount of 4.5 to 10. The pH can be controlled with acid (e.g., citric acid or benzoic acid) or base (e.g., sodium hydroxide) or buffered (with sodium citrate, benzoate, carbonate, or bicarbonate, disodium hydrogen phosphate, or sodium dihydrogen phosphate, for example).

In various embodiments, the aqueous oral composition (e.g., mouthrinse) contains a humectant. The humectant is generally a mixture of humectants, such as glycerin and sorbitol, and a polyhydric alcohol such as hexylene glycol, or polyethylene glycol, although the use of polyethylene glycol as a humectant in addition to its use to enhance the solubility of the active ingredient is optional. The humectant content typically is in the range of 5 to 40% and preferably 10 to 30%.

Surfactants suitable for compositions of the present invention include anionic, nonionic, and zwitterionic surfactants. The surfactant usually is present in the aqueous oral compositions of the present invention in an amount of 0.01% to 5%, preferably in an amount of 0.5% to 2.5%.

The oral composition according to the present invention may optionally include other materials, such as for example, cleaning agents, flavouring agents, sweetening agents, adhesion agents, surfactants, foam modulators, abrasives, pH modifying agents, humectants, moisturizers, mouth feel agents, colorants, abrasives, preservatives, fluoride ion source, saliva stimulating agents, emollients, viscosity modifiers, diluents, emulsifiers, nutrients and combinations thereof. Various components that may be added to the oral composition include, for example, a sweetening agent such as saccharin, or sodium saccharin, alcohols such as ethanol, fluoride ion sources such as sodium fluoride, as well as glycerine, sorbitol, polyethylene glycols, Poloxomer polymers such as POLOXOMER® 407, PLURONIC® F108, (both available from BASF Corporation), alkyl polyglycoside (APG), polysorbate, PEG40, castor oil, menthol, and the like. It is understood that while general attributes of each of the above categories of materials may differ, there may be some common attributes and any given material may serve multiple purposes within two or more of such categories of materials. Preferably, such carrier materials are selected for compatibility with the active ingredients found in *magnolia* extract or synthetic analogues thereof, as well as with other ingredients of the composition.

Flavorants among those useful herein include any material or mixture of materials operable to enhance the taste of the composition. Any orally acceptable natural or synthetic flavorant can be used, such as flavoring oils, flavoring aldehydes, esters, alcohols, similar materials, and combinations thereof. Flavorants include vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, and mixtures thereof. Also encompassed within flavorants herein are ingredients that provide fragrance and/or other sensory effect in the mouth, including cooling or warming effects. Such ingredients include menthol, menthyl acetate, menthyl lactate, camphor, eucalyptus oil, eucalyptol, anethole, eugenol, *cassia*, oxanone, [alpha]-irisone, propenyl guaiethol, thymol, linalool, benzaldehyde, cinnamaldehyde, N-ethyl-p-menthan-3-carboxamine, N,2,3-trimethyl-2-isopropylbutanamide, 3-1-menthoxypropane-1,2-diol, cinnamaldehyde glycerol acetal (CGA), methone glycerol acetal (MGA), and mixtures thereof. One or more flavorants are optionally present in a total amount of 0.01% to 5%, optionally in various embodiments from 0.05 to 2%, from 0.1% to 2.5%, and from 0.1 to 0.5%.

Sweetening agents among those useful herein include dextrose, polydextrose, sucrose, maltose, dextrin, dried invert sugar, mannose, xylose, ribose, fructose, levulose, galactose, corn syrup, partially hydrolyzed starch, hydrogenated starch hydrolysate, sorbitol, mannitol, xylitol, maltitol, isomalt, aspartame, neotame, saccharin and salts thereof, sucralose, dipeptide-based intense sweeteners, cyclamates, dihydrochalcones, and mixtures thereof.

Mouth-feel agents include materials imparting a desirable texture or other feeling during use of the composition.

Colorants among those useful herein include pigments, dyes, lakes and agents imparting a particular luster or reflectivity such as pearling agents. In various embodiments, colorants are operable to provide a white or light-colored coating on a dental surface, to act as an indicator of locations on a dental surface that have been effectively contacted by the composition, and/or to modify appearance, in particular color and/or opacity, of the composition to enhance attractiveness to the consumer. Any orally acceptable colorant can be used, including FD&C dyes and pigments, talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride, and mixtures thereof. One or more colorants are optionally present in a total amount of 0.001% to 20%, for example 0.01% to 10% or 0.1% to 5%.

In some embodiments, the oral composition of the present invention may comprise an optional abrasive useful for example as a polishing agent. Any orally acceptable abrasive can be used, but type, fineness, (particle size) and amount of abrasive should be selected so that tooth enamel is not excessively abraded in normal use of the composition. Suitable optional abrasives include silica, for example in the form of precipitated silica or as admixed with alumina, insoluble phosphates, calcium carbonate, and mixtures thereof. Among insoluble phosphates useful as abrasives are orthophosphates, polymetaphosphates and pyrophosphates. Illustrative examples are dicalcium orthophosphate dihydrate, calcium pyrophosphate, calcium pyrophosphate, tricalcium phosphate, calcium polymetaphosphate and insoluble sodium polymetaphosphate.

In some embodiments, the compositions of the present invention optionally comprise a tartar control (anticalculus) agent. Tartar control agents among those useful herein include salts of any of these agents, for example their alkali metal and ammonium salts: phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof.

In other embodiments, the oral compositions of the present invention optionally comprise a fluoride ion source, useful, for example, as an anti-caries agent. Any orally acceptable fluoride ion source can be used, including potassium, sodium and ammonium fluorides and monofluorophosphates, stannous fluoride, indium fluoride, amine fluorides such as olaflur (N'-octadecyltrimethylendiamine-N,N, N'-tris(2-ethanol)-dihydrofluoride), and mixtures thereof. One or more fluoride ion sources are optionally present in an amount providing a clinically efficacious amount of soluble fluoride ion to the oral composition.

In further embodiments, the oral compositions of the present invention optionally comprise a saliva stimulating agent useful, for example, in amelioration of dry mouth. Any orally acceptable saliva stimulating agent can be used, including without limitation food acids such as citric, lactic, malic, succinic, ascorbic, adipic, fumaric and tartaric acids, and mixtures thereof. One or more saliva stimulating agents are optionally present in saliva stimulating effective total amount.

In yet other embodiments, the oral compositions of the present invention optionally comprise a nutrient. Suitable nutrients include vitamins, minerals, amino acids, and mixtures thereof. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements include amino acids (such as L-tryptophane, L-lysine, methionine, threonine, levocarnitine and L-carnitine), lipotropics (such as choline, inositol, betaine, and linoleic acid), and mixtures thereof.

In some embodiments, the present invention provides a method of treating conditions associated with the presence of oral bacteria comprising providing an oral composition in accordance with any of the above-described embodiments, and applying the oral composition to the oral cavity of the mammalian subject. In some embodiments, the method comprises repeating the application of the composition multiple times until the desired anti-bacterial and/or anti-inflammatory effects are achieved in the subject.

As referred to herein, "inflammation" of the oral tissue generally refers to a localized protective response elicited by injury or destruction of tissues, which serves to destroy, dilute, or sequester both the injurious agent and the injured tissue. In the acute form, it is characterized by pain, heat, redness, swelling, and loss of function. Chronic inflammation is a slow process and primarily characterized by the formation of new connective tissue. Chronic inflammation is often a continuation of acute inflammation or a prolonged low-grade form of inflammation (such as that associated with periodontitis or gingivitis) and usually causes permanent tissue damage. Histologically, inflammation involves a complex series of events, including dilation of arterioles, capillaries, and venules, with increased permeability and blood flow; exudation of fluids, including plasma proteins, and leukocytic migration into the inflammatory locus. Inflammation corresponds to enhanced levels of proinflammatory cellular mediators, or substances that are released from cells, for example, as the result of the interaction of an antigen with an antibody or by the action of antigen with a sensitized lymphocyte.

In various embodiments, application or contacting is accomplished by rinsing, coating, brushing, or layering using appropriate dressing materials. In some embodiments, contacting also includes incidental contact during eating or chewing. In various embodiments, application of the composition comprises the use of an application device which aids in maintaining the contact time of the anti-inflammatory active ingredient comprising *magnolia* extract to the target tissue for a sufficient time as to allow the pharmacological inhibition of the elevated production of one or more inflammatory mediators, such as $PGE_2$ and TNF-$\alpha$.

In certain embodiments, an oral composition is not intentionally swallowed, but rather is retained in the oral cavity for a time sufficient to effect the intended utility. In other embodiments, particularly those where the oral composition is provided in an animal product, such as a pet food, pet food supplement (e.g., a treat), or a chew toy, the oral composition may be ingested at small concentrations which are not harmful to the animal. Preferably, specific materials and compositions to be used in this invention are pharmaceutically- or cosmetically-acceptable.

Some embodiments provide an oral composition comprising: from about 0.05 to about 10% by weight propylene glycol; from about 0.05 to about 5% by weight of one or more active ingredients found in *magnolia* extract or a synthetic analogue thereof; and an orally acceptable carrier.

Some embodiments provide a composition wherein at least one of one or more active ingredients is tetrahydromagnolol. In some embodiments, at least one of the one or more active ingredients is tetrahydrohonokiol. In other embodiments, at least one of the one or more active ingredients is 5,5'-di-n-butyl-biphenyl-2,2'-diol.

Some embodiments provide a method of treating a disease or condition of the oral cavity comprising: providing a composition comprising: from about 0.05 to about 10% by weight propylene glycol; from about 0.05 to about 5% by weight of one or more active ingredients found in *magnolia* extract or a synthetic analogue thereof; and an orally acceptable carrier; and applying the composition to the oral cavity of a subject in need thereof.

In some embodiments, the disease or condition of the oral cavity includes a disease or condition of the teeth, oral mucosa, gingiva or tongue. Such diseases or conditions include caries, gingivitis, periodontitis, and cosmetic conditions such as yellowing and malodour.

The invention will be described in greater detail by way of specific examples. The following examples are offered for illustrative purposes and are not intended to limit the scope of the invention in any manner. Those of skill in the art will readily recognize a variety of non-critical parameters which can be changed or modified to yield essentially the same results.

EXAMPLES

Oral compositions having the ingredients listed in the tables below can be prepared by the following method. Sodium fluoride and any other salts are dispersed in water. The humectants e.g., glycerin and sorbitol, are added to the mixture in a conventional mixer under agitation. The resultant mixture is agitated until a homogeneous gel phase is formed. A pigment such as $TiO_2$ is added into the gel phase and any acid or base (e.g., NaOH) required to adjust the pH to 6 to 7. Then organic thickeners, carrageenan, and CMC, are added. These ingredients are mixed until a homogenous phase is obtained. The mixture is then transferred to a high-speed vacuum mixer; where the silica abrasives, and the silica thickener are added. The mixture is then mixed at high speed for from 5 to 30 minutes, under vacuum of from about 20 to 50 mm of Hg, preferably about 30 mm Hg. The flavor oil is weighed and the *magnolia* extracts or their active ingredients are then added to the flavor oil. The flavor oil and *magnolia* actives are added to the mixture. Surfactants, such as sodium lauryl sulfate (SLS) are added last. The resultant product is a solublized, stable, efficacious, homogeneous, semi-solid, extrudable paste or gel product.

Example 1

A solubilized and efficacious oral composition containing propylene glycol and tetrahydrohonokiol, one of the active ingredients found in *magnolia* extract, is shown in Table 1.

TABLE 1

| Ingredient | Amount (%) |
| --- | --- |
| Purified water | 29 |
| Sorbitol | 19.45 |
| Glycerin | 20 |
| Sodium CMC-12 type USP | 1.1 |
| Iota carrageenan | 0.4 |
| Sodium saccharin-USP | 0.3 |
| Sodium fluoride | 0.24 |
| Zeodent-115 | 8.5 |
| Zeodent-165 | 3 |
| Sylodent XWA650 | 10 |
| Titanium dioxide | 0.5 |
| Sodium lauryl sulphate powder-NF | 1.5 |
| Flavor | 1 |
| Propylene glycol | 4.5 |
| Tetrahydrohonokiol | 0.5 |
| Total | 100 |

Example 2

A solubilized and efficacious oral composition containing propylene glycol and 5,5'-di-n-butyl-biphenyl-2,2'-diol, a structural analogue of magnolol, one of the active ingredients found in *magnolia* extract is shown in Table 2.

TABLE 2

| Ingredient | Amount (%) |
| --- | --- |
| Purified water | 29 |
| Sorbitol | 19.45 |
| Glycerin | 20 |
| Sodium CMC-12 type USP | 1.1 |
| Iota carrageenan | 0.4 |
| Sodium saccharin-USP | 0.3 |
| Sodium fluoride | 0.24 |
| Zeodent-115 | 8.5 |
| Zeodent-165 | 3 |
| Sylodent XWA650 | 10 |
| Titanium dioxide | 0.5 |
| Sodium lauryl sulphate powder-NF | 1.5 |
| Flavor | 1 |
| Propylene glycol | 4.5 |
| 5,5'-di-n-butyl-biphenyl-2,2'-diol | 0.5 |
| Total | 100 |

Example 3

A solubilized and efficacious oral composition containing propylene glycol and synthetic honokiol, one of the active ingredients found in *magnolia* extract is shown in Table 3.

TABLE 3

| Ingredient | Amount (%) |
| --- | --- |
| Purified water | 32.51 |
| Sorbitol | 19.45 |
| Glycerin | 20 |
| Sodium CMC-12 type USP | 1.1 |
| Iota carrageenan | 0.4 |
| Sodium saccharin-USP | 0.3 |
| Sodium fluoride | 0.24 |
| Zeodent-115 | 8.5 |
| Zeodent-165 | 3 |
| Zeodent-105 | 10 |
| Titanium dioxide | 0.5 |
| Sodium lauryl sulphate powder-NF | 1.5 |
| Flavor | 1 |
| Propylene glycol | 1 |
| Synthetic honokiol | 0.5 |
| Total | 100 |

Example 4

A solubilized and efficacious oral composition containing propylene glycol and natural honokiol, one of the active ingredients found in *magnolia* extract is shown in Table 4.

TABLE 4

| Ingredient | Amount (%) |
| --- | --- |
| Purified water | 33.96 |
| Sorbitol | 20 |
| Glycerin | 20 |
| Sodium CMC-12 type USP | 1.1 |
| Iota carrageenan | 0.4 |
| Sodium saccharin-USP | 0.3 |
| Sodium fluoride | 0.24 |
| Zeodent-115 | 7.5 |
| Zeodent-165 | 3 |
| Sylodent XWA 650 | 9 |
| Titanium dioxide | 0.5 |
| Sodium lauryl sulphate powder-NF | 1.5 |
| Flavor | 1 |
| Honokiol | 0.5 |
| Propylene glycol | 1 |
| Total | 100 |

Example 5

Table 5 (below) describes data demonstrating the effect of propylene glycol on the solubility of *magnolia* extract in a liquid formulation.

TABLE 5

| Ingredient | Formula 5A | Formula 5B | Formula 5C |
|---|---|---|---|
| Water | 41.04 | 40.95 | 40.07 |
| Sorbitol | 25.80 | 25.42 | 25.42 |
| Glycerin | 24.76 | 24.39 | 24.39 |
| Sodium fluoride | 0.30 | 0.29 | 0.29 |
| Sodium Sulphate | 0.62 | 0.61 | 0.61 |
| Gantrez Co-polymer | 2.80 | 2.75 | 2.75 |
| Sodium hydroxide | 0.75 | 0.74 | 0.74 |
| Sodium Saccharin | 0.38 | 0.37 | 0.37 |
| Sodium laurel sulphate | 1.87 | 1.84 | 1.82 |
| Flavor | 1.30 | 1.28 | 1.23 |
| Magnolia extract (>98% purity) | 0.39 | 0.38 | 0.37 |
| Propylene glycol | | 0.98 | 1.94 |
| Total | 100 | 100 | 100 |
| Formula appearance | Phase separation, creamy top layer | Translucent but homogeneous | Clear and transparent |

Example 6

Table 6 (below) describes data demonstrating the effect of propylene glycol on the solubility of magnolol in a liquid formulation.

TABLE 6

| Ingredient | Formula 6A | Formula 6B | Formula 6C |
|---|---|---|---|
| Water | 39.10 | 39.11 | 37.43 |
| Sorbitol | 24.04 | 24.04 | 23.73 |
| Glycerin | 23.07 | 23.07 | 22.77 |
| Sodium fluoride | 0.28 | 0.28 | 0.27 |
| Sodium Sulphate | 0.58 | 0.58 | 0.57 |
| Gantrez Co-polymer | 2.60 | 2.60 | 2.56 |
| Sodium hydroxide | 0.70 | 0.70 | 0.69 |
| Sodium Saccharin | 0.35 | 0.36 | 0.34 |
| Sodium lauryl sulphate | 2.21 | 1.72 | 1.7 |
| Flavor | 1.20 | 1.16 | 1.18 |
| Magnolol | 0.59 | 0.59 | 0.58 |
| Propylene glycol | 5.28 | 5.28 | 8.18 |
| Tauranol (additional surfactant) | | 0.51 | |
| Total | 100 | 100 | 100 |
| Formula appearance | Phase separation, creamy top layer | Phase separation, creamy top layer | Translucent but homogeneous |

Example 7

Table 7 (below) describes data demonstrating the effect of propylene glycol on the solubility of butyl magnolol in a liquid formulation.

TABLE 7

| Ingredient | Formula 7A | Formula 7B | Formula 7C | Formula 7D |
|---|---|---|---|---|
| Water | 40.86 | 40.23 | 39.49 | 38.00 |
| Sorbitol | 25.92 | 25.56 | 25.07 | 24.11 |
| Glycerin | 24.88 | 24.53 | 24.06 | 23.14 |
| Sodium fluoride | 0.30 | 0.29 | 0.29 | 0.28 |
| Sodium Sulphate | 0.63 | 0.62 | 0.6 | 0.58 |
| Gantrez Co-polymer | 2.80 | 2.76 | 2.71 | 2.61 |
| Sodium hydroxide | 0.75 | 0.74 | 0.73 | 0.70 |
| Sodium Saccharin | 0.37 | 0.37 | 0.36 | 0.35 |
| Sodium lauryl sulphate | 1.86 | 1.87 | 1.80 | 1.72 |
| Flavor | 1.26 | 1.21 | 1.18 | 1.15 |
| Butyl Magnolol | 0.38 | 0.37 | 0.37 | 0.37 |
| Propylene glycol | | 1.46 | 3.34 | 7.00 |
| Total | 100 | 100 | 100 | 100 |
| Formula appearance | Very Cloudy | Very Cloudy | Cloudy | Clear & transparent |

Example 8

Table 8 (below) describes data demonstrating the effect of propylene glycol on the solubility of propyl honokiol in a liquid formulation.

TABLE 8

| Ingredient | Formula 8A | Formula 8B | Formula 8C | Formula 8D |
|---|---|---|---|---|
| Water | 40.86 | 40.26 | 39.46 | 38.00 |
| Sorbitol | 25.92 | 25.54 | 25.05 | 24.12 |
| Glycerin | 24.87 | 24.51 | 24.04 | 23.15 |
| Sodium fluoride | 0.30 | 0.29 | 0.29 | 0.28 |
| Sodium Sulphate | 0.62 | 0.62 | 0.60 | 0.58 |
| Gantrez Co-polymer | 2.80 | 2.76 | 2.71 | 2.61 |
| Sodium hydroxide | 0.75 | 0.74 | 0.73 | 0.7 |
| Sodium Saccharin | 0.37 | 0.36 | 0.36 | 0.35 |
| Sodium lauryl sulphate | 1.86 | 1.83 | 1.79 | 1.73 |
| Flavor | 1.27 | 1.26 | 1.24 | 1.16 |
| Propyl Honokiol | 0.38 | 0.37 | 0.38 | 0.35 |
| Propylene glycol | | 1.46 | 3.35 | 6.97 |
| Total | 100 | 100 | 100 | 100 |
| Formula appearance | Very Cloudy | Clear & transparent | Clear & transparent | Clear & transparent |

Each patent, patent application, and printed publication, mentioned in this patent document is hereby incorporated by reference in its entirety.

As those skilled in the art will appreciate, numerous changes and modifications may be made to the embodiments described herein, without departing from the spirit of the invention. It is intended that all such variations fall within the scope of the claimed invention.

The invention claimed is:

1. An oral composition comprising:
   from about 0.05 to about 7% by weight propylene glycol;
   from about 0.05 to about 5% by weight of at least one or more active ingredients found in *magnolia* extract or a synthetic analogue thereof, selected from honokiol and tetrahydrohonokiol; and
   an orally acceptable carrier; wherein the composition is a semi-solid paste or gel or is a liquid formulation, and wherein the amount of the propylene glycol in the composition is sufficient to enhance the solubility of the active ingredient therein.

2. The oral composition of claim 1, wherein the propylene glycol is present in an amount from 0.1% to 5% by weight of the oral composition.

3. The oral composition of claim 2, wherein at least one of the one or more active ingredients is present in an amount from 0.1% to 3% by weight of the composition.

4. The oral composition of claim 3, wherein at least one of the one or more active ingredients is honokiol.

5. The oral composition of claim 3, wherein at least one of the one or more active ingredients is tetrahydrohonokiol.

6. The oral composition of claim 4, wherein the honokiol is synthetic honokiol.

7. A method of treating or preventing a disease or condition of the oral cavity comprising:
provemed the oral composition of claim 1 and
applying the oral composition to the oral cavity of a subject in need thereof.

8. The method of claim 7, wherein the oral composition is applied daily for a period of at least one week.

9. The composition of claim 1, wherein the composition is a liquid formulation.

10. The composition of claim 1, wherein the composition is a semi-solid paste or gel.

* * * * *